(12) United States Patent
Slotman

(10) Patent No.: US 11,974,814 B2
(45) Date of Patent: May 7, 2024

(54) SYSTEM AND METHOD FOR SELECTING AND IMPLEMENTING A BARIATRIC SURGERY

(71) Applicant: THE S.M.A.R.T. CORPORATION, Morrestown, NJ (US)

(72) Inventor: Gus J. Slotman, Moorestown, NJ (US)

(73) Assignee: The S.M.A.R.T. Corporation, Moorestown, NJ (US)

( * ) Notice: Subject to any disclaimer, the term of this patent is extended or adjusted under 35 U.S.C. 154(b) by 483 days.

(21) Appl. No.: 17/490,444

(22) Filed: Sep. 30, 2021

(65) Prior Publication Data

US 2022/0015834 A1 Jan. 20, 2022

Related U.S. Application Data

(63) Continuation-in-part of application No. 15/223,881, filed on Jul. 29, 2016, now abandoned, which is a continuation-in-part of application No. 14/258,464, filed on Apr. 22, 2014, now abandoned.

(60) Provisional application No. 61/815,799, filed on Apr. 25, 2013.

(51) Int. Cl.
| | |
|---|---|
| *A61B 34/10* | (2016.01) |
| *G16H 10/60* | (2018.01) |
| *G16H 20/40* | (2018.01) |
| *G16H 50/20* | (2018.01) |
| *G16H 50/70* | (2018.01) |

(52) U.S. Cl.
CPC ............ *A61B 34/10* (2016.02); *G16H 10/60* (2018.01); *G16H 20/40* (2018.01); *G16H 50/20* (2018.01); *G16H 50/70* (2018.01)

(58) Field of Classification Search
CPC ........ G16H 20/60; G16H 50/70; G16H 50/20; G16H 50/50; G16H 10/60; A61N 1/36085
See application file for complete search history.

(56) References Cited

U.S. PATENT DOCUMENTS

| | | | |
|---|---|---|---|
| 7,194,301 B2 | 3/2007 | Jenkins et al. | |
| 8,036,912 B2 | 10/2011 | Jensen et al. | |
| 2005/0080462 A1 | 4/2005 | Jenkins et al. | |
| 2007/0244375 A1* | 10/2007 | Jenkins | A61N 1/36085 600/301 |
| 2014/0324446 A1 | 10/2014 | Slotman | |

FOREIGN PATENT DOCUMENTS

| | | |
|---|---|---|
| WO | 2005038693 A1 | 4/2005 |
| WO | 2014047388 A9 | 3/2014 |
| WO | WO-2014047388 A1 * | 3/2014 ............... G01N 5/04 |

OTHER PUBLICATIONS

Chau et al. (2005) "Patient Characteristics Impacting Excess Weight Loss Following Laparoscopic Adjustable Gastric Banding," Obesity Surgery 15:346-350.
Nabnet et al. (2010) "Comparison of 30-Day Outcomes After Non-Lap Band Primary and Revisional Bariatric Surgical Procedures from the Longitudinal Assessment of Bariatric Surgery Study," Surgery for Obesity and Related Diseases 6:22-30.
Lutfi et al. (2006) "Predictors of Success After Laparoscopic Gastric Bypass: a Multivariate Analysis of Socioeconomic Factors," Surgical Endoscopy 20:864-867.
Office Communication dated Jul. 2, 2014 in U.S. Appl. No. 14/258,464, filed Apr. 22, 2014.
Office Communication dated Nov. 14, 2014 in U.S. Appl. No. 14/258,464, filed Apr. 22, 2014.
Office Communication dated Mar. 6, 2015 in U.S. Appl. No. 14/258,464, filed Apr. 22, 2014.
Office Communication dated May 21, 2015 in U.S. Appl. No. 14/258,464, filed Apr. 22, 2014.
Office Communication dated Feb. 5, 2016 in U.S. Appl. No. 14/258,464, filed Apr. 22, 2014.
Office Communication dated Aug. 7, 2018 in U.S. Appl. No. 15/223,881, filed Jul. 29, 2016.
Office Communication dated Apr. 11, 2019 in U.S. Appl. No. 15/223,881, filed Jul. 29, 2016.
Patent Trial and Appeal Board Decision dated Jul. 30, 2021 in U.S. Appl. No. 15/223,881, filed Jul. 29, 2016.
Piaggi et al. (2010) "Artificial Neural Networks in the Outcome Prediction of Adjustable Gastric Banding in Obese Women," PLoS ONE 5(10):e13624.
Ramanan et al. (2012) "Development and Validation of a Bariatric Surgery Mortality Risk Calculator," Journal of the American College of Surgeons 214:892-900.
Schienkiewitz et al. (2012) "Comorbidity of overweight and obesity in a nationally representative sample of German adults ages 18-79 years," BMC Public Health 12:658.
Turner et al. (2011) "A Nomogram for Predicting Surgical Complications in Bariatric Surgery Patients," Obesity Surgery 21:655-662.
Valera-Mora et al. (2005) "Predictors of weight loss and reversal of comorbidities in malabsorptive bariatric surgery," Am. J. Clin. Nutr. 81:1292-7.

* cited by examiner

*Primary Examiner* — Joseph D Burgess
(74) *Attorney, Agent, or Firm* — Licata & Tyrrell P.C.

(57) ABSTRACT

This invention relates to a method and network system for selecting an appropriate bariatric surgery for a patient based upon baseline patient parameters.

3 Claims, No Drawings

SYSTEM AND METHOD FOR SELECTING AND IMPLEMENTING A BARIATRIC SURGERY

INTRODUCTION

This application is a continuation-in-part application of U.S. application Ser. No. 15/223,881, filed Jul. 29, 2016, which is a continuation-in-part application of U.S. application Ser. No. 14/258,464, filed Apr. 22, 2014, which claims the benefit of U.S. Provisional Application No. 61/815,799, filed Apr. 25, 2013, the contents of which are incorporated herein by reference in their entireties.

BACKGROUND

Obesity is a complex medical disorder of appetite regulation and metabolism resulting in excessive accumulation of adipose tissue mass. Typically defined as a body mass index (BMI) of 30 kg/m$^2$ or more, obesity is a world-wide public health concern that is associated with cardiovascular disease, diabetes, certain cancers, respiratory complications, osteoarthritis, gallbladder disease, decreased life expectancy, and work disability. The primary goals of obesity therapy are to reduce excess body weight, improve or prevent obesity-related morbidity and mortality, and maintain long-term weight loss.

Treatment modalities typically include lifestyle management, pharmacotherapy, and surgery. Treatment decisions are made based on severity of obesity, seriousness of associated medical conditions, patient risk status, and patient expectations. Notable improvements in cardiovascular risk and the incidence of diabetes have been observed with weight loss of 5-10% of body weight, supporting clinical guidelines for the treatment of obesity that recommend a target threshold of 10% reduction in body weight from baseline values.

However, while prescription anti-obesity medications are typically considered for selected patients at increased medical risk because of their weight and for whom lifestyle modifications (diet restriction, physical activity, and behavior therapy) alone have failed to produce durable weight loss, approved drugs have had unsatisfactory efficacy for severely obese subjects, leading to only ~3-5% reduction in body weight after a year of treatment.

Bariatric surgery may be considered as a weight loss intervention for patients at or exceeding a BMI of 40 kg/m$^2$. Patients with a BMI35 kg/m$^2$ and an associated serious medical condition are also candidates for this treatment option. Devices currently being used for weight-loss intervention and treatment include gastric bands (e.g., the LAP-BAND APO Adjustable Gastric Banding System), electrical stimulation systems that block nerve activity between the brain and stomach (e.g., the Maestro Rechargeable System), gastric balloon systems (e.g., the ORBERA® Intragastric Balloon System or OBALON® Balloon System), transpyloric bulbs (e.g., the TransPyloric shuttle), and gastric emptying systems (e.g., ASPIREASSIST®). Unfortunately, postoperative complications commonly result from bariatric surgical procedures, including bleeding, embolism or thrombosis, wound complications, deep infections, pulmonary complications, and gastrointestinal obstruction; reoperation during the postoperative period is sometimes necessary to address these complications. Rates of reoperation or conversion surgery beyond the postoperative period depend on the type of bariatric procedure and can range from 17% to 31%. Intestinal absorptive abnormalities, such as micronutrient deficiency and protein-calorie malnutrition, also are typically seen with bypass procedures, requiring lifelong nutrient supplementation. Major and serious adverse outcomes associated with bariatric surgery are common, observed in approximately 4 percent of procedures performed (including death in 0.3 to 2 percent of all patients receiving laparoscopic banding or bypass surgeries, respectively).

Given the risks associated with bariatric surgery, it would be of significant benefit to know the outcome of a bariatric surgery prior to conducting the surgery. The present invention meets this need in the art.

SUMMARY OF THE INVENTION

The present invention is a computer-implemented method for selecting and implementing a patient-specific bariatric surgery, which includes receiving a baseline data set of a patient, the baseline data set including at least age, comorbidities, and employment for the patient; comparing the patient data set to a plurality of reference patient data sets to identify similar patient data sets in the plurality of reference patient data sets, wherein said comparison includes linear regression modeling of independent variables for weight and weight loss as dependent variables, and logistic regression modeling of independent variables for comorbidities as dependent variables, wherein the independent variables include at least one of age or employment and the reference patient data sets include patients receiving treatments with a plurality of bariatric surgeries; identifying similar patient data sets from the reference patient data sets including a target treatment outcome associated with the plurality of bariatric surgeries; calculating, for each of the plurality of bariatric surgeries, a probability of achieving the target treatment outcome for the patient; and selecting and implementing at least one of the plurality of bariatric surgeries for the patient, based on the calculated probability of achieving the target treatment outcome. In some embodiments, the selection of a surgery includes the selection of a bariatric surgery device, e.g., an adjustable gastric band, intragastric balloon, transpyloric bulb, gastric emptying device, or electrical stimulator. In other embodiments, the comorbidities are diabetes mellitus, hypertension, obstructive sleep apnea, liver disease, GERD, cholelithiasis, abdominal hernia, or congestive heart failure.

The invention also includes a system for selecting and implementing a patient-specific bariatric surgery for a patient, the system including one or more processors; and a memory storing instructions that, when executed by the one or more processors, cause the system to perform operations including: receiving a baseline data set of a patient, the baseline data set including at least age, comorbidities, and employment for the patient; comparing the patient data set to a plurality of reference patient data sets to identify similar patient data sets in the plurality of reference patient data sets, wherein said comparison comprises linear regression modeling of independent variables for weight and weight loss as dependent variables, and logistic regression modeling of independent variables for comorbidities as dependent variables, wherein the independent variables comprise at least one of age or employment and wherein the reference patient data sets comprise patients receiving treatments with a plurality of bariatric surgeries; identifying similar patient data sets from the reference patient data sets comprising a target treatment outcome associated with the plurality of bariatric surgeries; calculating, for each of the plurality of bariatric surgeries, a probability of achieving the target treatment outcome for the patient; and selecting at least one of the plurality of bariatric surgeries for the patient, based on the calculated probability of achieving the target treatment outcome.

DETAILED DESCRIPTION OF THE INVENTION

It has now been found that individual patient weight, weight loss, presence or absence of co-morbidities, and adverse events up to 24 months after open gastric bypass (ORYGB), laparoscopic gastric bypass (LRYGB), adjustable gastric band (AGB), duodenal switch (DS), and sleeve gastrectomy (SLEEVE) can be predicted from baseline pre-operative data from an individual patient. Using the present invention, demographic, physiologic and medical information about morbidly obese subjects can be entered into the models described herein and surgery outcome can be obtained prior to open gastric bypass, laparoscopic gastric bypass, adjustable gastric banding, sleeve gastrectomy, or duodenal switch surgery. Alternatively stated, using the method of this invention, it can be determined prior to surgery how much weight the subject would lose and whether or not co-morbidities such as sleep apnea, hypertension, diabetes, GERD, and the like will resolve with surgical intervention, thus allowing the subject and the subject's surgeon to choose objectively which operation and bariatric surgical devices would be best for the subject. Indeed, resolution of diabetes mellitus was predicted with a 24 month specificity of 93.97% as was its persistence at clinically applicable sensitivities. Similarly, hypertension prognostications matched observed results at consistently high sensitivity/specificity. Models that predicted obstructive sleep apnea were validated with specificities greater than 90% through 24 months. Pre-operative predictions of the development and resolution of liver disease also carried strong predicted versus observed agreement. Cholelithiasis models were validated at highly reproducible levels through 24 months. Individual patients resolving GERD were identified in advance from pre-operative data. Abdominal hernia in individual patients was predicted with excellent sensitivity and specificity. In this respect, a subject can decide which surgery is most appropriate for him or her based on weight loss predictions, predicted resolution of co-morbidities the subject had at baseline, and predictions of post-operative adverse events, i.e., complications. These predicted outcomes can be taken into consideration individually or together to select and implement the appropriate surgery and device for the subject.

While previous reports have described simple formulas (Sczepaniak, et al. (2012) J. Obesity Article ID 195251), validated quartile regression curves (Geloneze, et al. (2012) Int. J. Obes. (Lond) 36(3):363-8), artificial neural networks (Piaggi, et al. (2012) PLoS ONE 5:e13624; Wise, et al. (2016) Surg. Endosc. 30(2):480-8; Campos, et al. (2008) Arch. Surg. 143:877-84) and other correlations (Saranya, et al. (2015) J. Obes. Metab. Res. 2:16-21; Slotman (2002) Crit. Care Med. 30:1035-45; Barhouch, et al. (2015) Obes. Surg. 26(6):1178-85; Ortega, et al. (2012) Surg. Endosc. 26; 1744-50; Parri, et al. (2015) Nutr. Clin. Prac. 30:420-4) to predict weight loss probability from single institution experiences, published models have been applied to only one operation, have not validated continuous models prospectively, and have used databases much smaller and less broadly representative than the BOLD population of the present study. Others associated early post-operative weight loss with later outcomes (Manning, et al. (2015) Surg. Endosc. 29:1484-91; Raisdana & Slotman (2014) Crit. Care Med. 41:542), which did not aid pre-operative selection of the best operation. Baseline models in the present analyses achieved Pearson correlation coefficients of 0.959, 0.932, 0.875, 0.837, and 0.811 at 2, 6, 12, 18, and 24 months post-operative, respectively, for predicted versus observed weight and weight loss, comparing the five most popular bariatric operations. The results herein make possible for the first-time data-based individual choice of the best weight loss operation. Advance knowledge of this accuracy can facilitate pre-operative decision-making for individual morbidly obese patients.

Type II diabetes mellitus is active in 28-52% of bariatric surgery patients. While diabetes improves in most patients with weight loss, knowing what the resolution rate will be after each of the available operations could increase patients' confidence in choosing surgery. Modeling on BOLD patients in the present study predicted pre-operatively the resolution or presence of Type II diabetes mellitus for individual patients 24 months in advance at clinically helpful levels of accuracy. Diabetes model fit ranged from ROC/AUC 0.956 at 2 months to 0.926 at 24 months after surgery. Validation diabetes sensitivity was 98% to 60%, with specificity consistently above 91%. Previous studies have associated the treatment of diabetes with post-operative weight loss, without predicting actual diabetes outcomes (Yska, et al. (2015) JAMA Surg. 150:1126-33; Saranya, et al. (2015) J. Obes. Metab. Res. 2:16-21; Lee, et al. (2009) Hepatogastroenterology 56(93):1222-6; Zenti, et al. (2015) Acta Diabetol. 52:937-942). Non-validated investigations correlated pre-operative age, sex, HbA1c, waist circumference, C-peptide, BMI, duration of diabetes, fasting glucose, lack of insulin use, and type of procedure with post-operative diabetes, but useable prognostications were not generated (Adams, et al. (2013) Postgrad. Med. J. 89:411-416; Robert, et. al. (2013) Obes. Surg. 23:770-775; Panunzi, et al. (2015) Ann. Surg. 261:459-467; Still, et al. (2014) Lancet Diabetes Endocrinol. 2(1):38-45). The prognostic models reported herein enable morbidly obese patients with Type II diabetes to know in advance what their relative probability of disease remission will be 24 months in advance, and are not limited to a single procedure, comparing future individual diabetes outcomes from five weight loss operations.

Arterial hypertension, an important weight-related medical problem, resolves frequently following bariatric surgery. However, prior to the present analyses, remission or persistence of hypertension after any weight loss procedure was not predicted, but rather, only associated statistically with age, severity of hypertension, number of anti-hypertension medications, diuretic use, and post-operative weight loss (Kolotkin, et al. (2011) Surg. Obes. Relat. Dis. 7:605-610). The present analysis describes accurate, prospectively validated models that predict, from pre-surgical data and up to 24 months in advance, the risk of hypertension for individual patients, comparing possible future outcomes for ORYGB, LRYGB, SLEEVE, AGB and DS. Model ROC/AUC was 0.913 at 2 months and 0.858 at 24 months. Validation sensitivity/specificity were 92.44%/85.21% at 2 months and 79.56%/79.3% at 24 months. For the first time, these results enable hypertensive morbidly obese patients to choose objectively which procedure will benefit each most.

Obstructive sleep apnea affects more that 40% of morbidly obese patients who choose bariatric surgery (46, 55), and many patients see their OSA resolve following weight loss surgery (56). Nevertheless, investigations that predict outcomes for OSA in the post-operative period are rare. For example, Letteri et al (57) observed that the severity of pre-operative OSA itself was the strongest predictor of its persistence in bariatric surgery follow-up. Models that predicted OSA outcomes in the present paper performed well, with all ROC/ACU values 0.827 and higher. Predicted versus observed sensitivity/specificity ranged from 73.99%/93.6% at 2 months, to 50.76%/90.95% at 24 months. While sensitivities for late OSA persistence may have been suboptimal, pre-operative prognostication of OSA resolution was clinically reliable. Our review of the literature indicates that such validated advance knowledge of OSA outcomes in individual bariatric surgery patients, again comparing five operations, has not been reported previously, and is a significant finding of this study.

Non-alcoholic fatty liver disease and non-alcoholic steatohepatitis afflict many morbidly obese patients. Serious weight-related liver disease is diagnosed in 7-16% of patients who present for bariatric surgery. While liver disease resolves frequently with weight loss, outcomes do vary between LRYGB, AGB, SLEEVE, and DS, adding decisional uncertainty to each affected patient regarding which operation to undergo. For these patients, the liver disease models in this study add objectivity to the choice of bariatric procedure. Model fit ROC/AUC values all were 0.940 and above. Median liver disease sensitivity/specificity was 84.79%/98.41%. Thus, although the diagnosis of liver disease in BOLD was clinical only, as liver biopsies were not required on all patients, the prognostic models here provide individual weight-related liver dysfunction patients with clinically significant guidance regarding predicted outcomes by operation.

At the time of bariatric surgery, 9-31% of patients have gallstones, and the incidence of cholelithiasis increases with post-operative weight loss. However, the literature has not identified pre-operative factors that predict the incidence of cholelithiasis following bariatric surgery. Rapid post-operative weight lost has been the only consistently published risk factor (Li, et al. (2009) *Surg. Endosc.* 23:1640-4; Abo-Ryia, et al. (2014) *Surg. Sci.* 5:1-5; Naik, et al. (2015) *Nat. Rev. Gastroenterol. Hepatol.* 13(2):111-9). In this investigation, cholelithiasis modeling from pre-operative data performed well with ROC/AUC's all at 0.949 and higher. Validation of actual predicted versus observed results yielded sensitivity/specificity above the 86.93%/97.21% level through 24 months. These models provide patients and surgeons a means of identifying patients most at risk for gallstone formation. This advance knowledge could facilitate the decision of whether or not to perform incidental cholecystectomy at the time of primary bariatric surgery, or, for high-risk patients without gallstones at the time of bariatric surgery, medical intervention.

GERD is diagnosed pre-operatively in 35-52% of patients who undergo bariatric surgery. Resolution of GERD is excellent with ORYGB/LRYGB, and DS, variable with AGB, but GERD may increase following SLEEVE. No prior investigation has assessed risk of resolution or persistence or progression of GERD in individual patients after weight loss operations. GERD model fit reported here ranged from ROC/AUC 0.898 to 0.804. While sensitivity (positive prediction) drifted below 50% at 12 months, specificity (GERD resolution) actually increased in the 12-24-month models. Considering the inter-procedure variation of bariatric surgeries regarding post-operative GERD, the advance knowledge presented in this study may enable patients to compare the GERD effects of each technique in their individual cases.

At least 8% of bariatric surgery patients have pre-existing inguinal and ventral abdominal wall hernias, and how and when to repair these defects continues to be debated. However, the incidence of abdominal hernia can increase following bariatric surgery to 50% and higher. The prognostic models reported here provide patients and surgeons reliable pre-operative predictions of abdominal hernia development in individuals, again comparing the five most common weight loss procedures. With ROC/AUC all 0.921 and higher, and sensitivity/specificity consistently at clinically useful levels, these findings can facilitate objective pre-operative bariatric surgery planning regarding relative risk of abdominal hernia.

Congestive heart failure (CHF) affects up to 9% of bariatric surgery patients pre-operatively. Although weigh loss logically should ameliorate CHF severity, the rate of CHF following bariatric surgery can increase to over 22%. The ability to identify before surgery the individuals most at risk for CHF months and years after weight loss operations certainly could assist in pre-operative planning and peri-surgical management. In the present work, CHF ROC/AUC model fit was excellent. However, although specificity was above 99%, marking patients who will not suffer CHF, low event rates kept sensitivities and the identification of CHF risk patients in the 40% range and below. Nevertheless, these results are the first reported predictions of CHF in bariatric surgery and provide positive predictions much greater than the actual incidence of CHF post-operatively.

Close long-term follow-up with bariatric surgeons and staff and regular support group attendance help to optimize surgical outcomes. Travel distance, anxiety levels, race, sex, early weight loss age, BMI, marital status, employment status, OSA, diabetes, and health insurance have been associated with medical and support group follow-up. In the present investigation, pre-operative modeling ROC/ADC's were 0.620 and under, Specificity was above 99%, but Sensitivity was <1%. In this modeling, then, one knows before surgery who will not follow-up, but not who are the compliant patients. Perhaps this identifies, at least, pre-operatively the patients who need the most encouragement for follow-up compliance.

The continuous variable models described here provide individual morbidly obese patients clinically accurate predictions of what weight and weight loss would be for each of them up to 24 months in advance, comparing results after ORYGB, LRYGB, AGB, SLEEVE, and DS. Categorical models generated reliable relative risk prognostications for the presence/absence of diabetes, hypertension, OSA, liver disease, cholelithiasis, GERD, and abdominal hernia, accurately predicting outcomes for individuals among the five operations investigated. These results can enable severely overweight patients and their families, physicians and surgeons to know, before a bariatric procedure and device is selected, which operation, relative to the others, would be best for each. Such advance knowledge can improve bariatric surgery outcomes through matching patients to the individually most appropriate operations objectively.

Having demonstrated that baseline parameters such as weight, weight loss, presence or absence of co-morbidities, and adverse events can be used to predict target treatment outcomes for bariatric surgery, the present invention can be used in selecting or prescribing and implementing an appropriate surgical approach for a morbidly obese patient considering weight loss intervention via bariatric surgery. In accordance with the method of this invention, a bariatric surgery is selected and implemented by receiving a baseline data set of a patient, in particular at least age, comorbidities, and employment for the patient; comparing the patient data set to a plurality of reference patient data sets to identify similar patient data sets in the plurality of reference patient data sets, wherein said comparison includes linear regression modeling of independent variables for weight and weight loss as dependent variables, and logistic regression modeling of independent variables for comorbidities as dependent variables, wherein the independent variables include at least one of age or employment and wherein the reference patient data sets include patients each of which have received treatment with at least one of a plurality of bariatric surgeries; identifying similar patient data sets from the reference patient data sets including a target treatment outcome (e.g., weight loss and/or resolution of one or more comorbidities) associated with the plurality of bariatric surgeries; calculating, for each of the plurality of bariatric surgeries, a probability of achieving the target treatment outcome for the patient; selecting and implementing at least one of the plurality of bariatric surgeries for the patient, based on the calculated probability of achieving the target treatment outcome. In some aspects, the target treatment outcome is weight loss. In other aspects, the target treatment outcome is resolution of one or more comorbidities. In further aspects, the target treatment outcome is weight loss and resolution of one or more comorbidities.

Patient baseline data sets are generated from one or more baseline parameters. Patient parameters, for purposes of this invention, may include demographics, comorbidities, medications, procedures, weight loss and maintenance, physiological variables, and complications.

Exemplary demographic variables which may be selected for inclusion in a patient profile include, but are not limited to, age, sex, or race. Comorbidities particularly include cholelithiasis (i.e., a subject with asymptomatic gallstones as well as symptomatic gallstones), gastroesophageal reflux disease (GERD), diabetes or a glucose metabolism disorder, hypertension, chronic heart failure (CHF), liver disease (e.g., a subject who has had a hepatomegaly or non-normal liver function test), obstructive sleep apnea (e.g., sleep apnea requiring oral appliance, significant hypoxia, or oxygen-dependence), abdominal hernia (e.g., any history of symptomatic or asymptomatic abdominal hernia). Comorbidities can also include, e.g., alcohol abuse, HIV, dialysis, neutropenia, solid tumors, hematologic malignancies, chronic renal failure, abdominal skin pannus, angina, BMI, back pain, DVT/PE, depression, fibromyalgia, or gout.

Examples of physiologic variables which may be selected for inclusion in a patient profile include, but are not limited to, physical examination, vital signs, and clinical laboratory tests. More specifically, physiologic variables selected may include height, weight, temperature, MAP, heart rate, diastolic blood pressure, and systolic blood pressure of the patient. In addition, complete blood count, platelet count, prothrombin time, partial thromboplastin time, fibrin degradation products and D-dimer, serum creatinine, lactic acid bilirubin, AST, ALT, and/or GGT can be measured. Heart rate, respiratory rate, blood pressure and urine output can also be monitored. Chest X-rays and bacterial cultures can also be performed as clinically indicated.

In particular embodiments, the baseline parameters include age, height (cm), abdominal hernia, hypertension, African American, operation, alcohol use, liver disease, angina, mental health diagnosis, asthma, musculoskeletal pain, back pain, obesity, hypoventilation syndrome, congestive heart failure, psychological impairment, Caucasian, employment status, pulmonary hypertension, cholelithiasis, stress urinary incontinence, depression, weight (kg), GERD and gender.

Some or all of these patient parameters are preferably determined at baseline (i.e., before intervention), and daily thereafter where applicable, and are entered into a network system and a patient data set comprising one or more of the patient parameters is generated. The network system includes a processor that runs one or more statistical tests and compares the baseline parameters of the patient with reference patient data sets (electronically stored in the network's memory) including independent variables for subjects who have responded positively to bariatric surgeries (e.g., exhibited weight loss and/or resolution of one or more comorbidities). Based upon comparisons with the reference patient data sets, the processor identifies similar patient data sets from the reference patient data sets and calculates, for each of the plurality of bariatric surgeries, a probability of achieving the target treatment outcome for the patient. Using the calculated probability, the clinician can select and implement a bariatric surgery, e.g., a particular device, that is appropriate for the patient so that a target treatment outcome is achieved, e.g., a target weight loss or resolution of one or more comorbidities.

As one of skill in the art will appreciate from this disclosure, as patient data sets are generated for more patients and additional data are collected for these parameters, it may be found that some parameters in this list of examples are less predictive than others. Those parameters identified as less predictive in a larger patient population need not be included in all patient profiles. In this respect, certain embodiments of the present invention include combining or entering the patient baseline parameters and post-operative outcome into the network memory containing a collection of patient baseline parameters and outcomes, which in turn are used in the generation of one or more control profiles.

For purposes of this invention, a "reference patient data set" can be generated from a database containing mean values for selected patient parameters from a population of patients. A reference patient data set for selecting and implementing an appropriate bariatric surgery is a reference patient data set, as defined supra, that includes independent variables linked to a treatment identified to be effective in those patients with similar conditions from which the reference patient data set was generated.

As will be understood by those of skill in the art upon reading this disclosure, patient data sets can be generated from all of the patient parameters discussed supra. Alternatively, patient data sets can be based upon only a portion of the patient parameters. Since the patient parameters for each patient, as well as the reference patient data sets, are stored in a database, various patient data sets comprising different patient parameters can be generated for a single patient and compared to an established reference patient data set comprising the same parameters. The ability of these various data sets to be predictive can then be determined via statistical analysis.

Continuous, normally distributed variables are evaluated using analysis of variance. When appropriate, statistical comparisons between subgroups are made using the t-test or the chi-squared equation for categorical variables. Data analysis and/or comparisons are carried out by a processor of the network system with results or output available on a monitor, printout or other readout. In particular embodiments, the generated outcome is visually displayed and, as shown herein, provides comparisons of calculated probabilities for target treatment outcomes for a plurality of bariatric surgeries.

Models for continuous variables were built using linear regression. Logistic Regression was used to find the best predictors to examine dichotomous variables adverse events at 0, 0-6 and 0-12 months and co-morbidities at 2, 6, 12, 18 and 24 months. All models were built using forward selection to choose the independent variables that would best predict the individual outcome. All interactions were examined between treatment and the other independent variables, significant interactions with treatment remained in the model. Independent categorical variables with a low incidence rate were collapsed to create larger groups. Independent variables, used in the logistic regression models, that caused a quasi-complete separation of data points due to a low incidence rate were not used in any of the models. When the modeling process was completed, models were validated prospectively by entering baseline information from the patients in the validation group into the models and then comparing the predicted results to the actual observed outcomes. To examine model fit, for the linear regression models, the coefficient of determination (r2) was examined and for dichotomous dependent variables by Receiver Operating Characteristics/Area Under the Curve (ROC/AUC) were examined for the model set.

After the modeling process was completed, baseline, pre-operative data, which fulfilled requirements for the models from the validation group, were entered into each model. Sensitivity and specificity assessed predicted versus observed correlations for dichotomous dependent variables. Pearson Correlation coefficient evaluated continuous dependent variables.

The physician or another individual of skill in the art uses the patient data set as a guide to select or prescribe a bariatric surgery/device selected from gastric bypass, laparoscopic gastric bypass, adjustable gastric band, duodenal switch, and sleeve gastrectomy based upon whether the patient profile matches the reference patient data set of the bariatric surgery. This method is therefore a way to enhance the likelihood of a positive or successful bariatric surgery outcome. A positive outcome for a bariatric surgery can include weight loss, reduced morbidity, resolution of one or more comorbidities, and/or reduced adverse events.

Example 1: Methods

HIPAA-compliant data was analyzed from the Surgical Review Corporation's Bariatric Outcomes Longitudinal Database (BOLD) (DeMaria, et al. (2010) *Surg. Obes. Relat. Dis.* 6:347-355) on 166,601 patients who had undergone, as their primary bariatric procedure, one of five different bariatric operations over a 3-year period, and who had had at least one post-operative follow-up visit. Patients undergoing revisional bariatric surgery were excluded. In the overall population, 5,389 patients underwent ORYGB, 83,059 had LRYGB, 8,966 received SLEEVE, 67,514 had an AGB inserted, and 1,673 had DS. Subjects were randomized into a modeling group (n=124,053) or a validation group (n=42, 548). Pre-operative BOLD parameters for which less than 5% of the data was missing (n=46) were screened as possible weighted independent variables. Categorical pre-operative variables were sub-categorized by severity of illness in BOLD using semi-numerical scales of 1 to 5 or 1 to 4, etc. These sub-categories were included in the statistical mix. Continuous dependent variables included weight and weight loss. Dichotomous dependent variables included diabetes mellitus, hypertension, obstructive sleep apnea (OSA), liver disease, cholelithiasis, gastrointestinal reflux disease (GERD), congestive heart failure, abdominal hernia, surgeon/support group follow-up and adverse events. These conditions were diagnosed according to clinical criteria specified by the Surgical Review Corporation's BOLD database reporting definitions (DeMaria, et al. (2010) *Surg. Obes. Relat. Dis.* 6:347-355).

From a General Estimating Equation platform, multivariate linear regression identified baseline, pre-operative variables that best predicted weight and weight loss at each post-operative observation time point (2, 6, 12, 18 and 24 months) for each operation. Multivariate logistic regression identified pre-operative independent parameters to predict dichotomous dependent variables, including co-morbidities at 2, 6, 12, 18 and 24 months for each operation, and adverse events at 0-6, and 0-12 months. All models were built using forward selection. Interactions were examined between treatment and the other independent variables and were included in the model if the interaction coefficient had p<0.10. Variables that caused a quasi-complete separation of data points due to low incidence rates were not used. To examine model fit for the linear regression models, the coefficient of determination ($r^2$) was calculated. Model fit for dichotomous dependent variables was assessed by Receiver Operating Characteristics/Area Under the Curve (ROC/AUC) calculations for each model set. (Lee, et al. (2009) *Hepatogastroenterology* 56(93):1222-6) Modeling was performed for each operation for each dependent variable at each observation point.

After the best predictors for the model were selected, the linear models were tested by calculating the predicted values for the validation group and comparing them to the actual observed outcomes by examining Pearson correlation coefficients. For the logistic models, sensitivity and specificity were examined for predicted versus observed results of dichotomous dependent variables from individual validation group patients.

Example 2: Pre-Operative Prediction of Weight Loss and Co-Morbidity Resolution

Pre-operative variables that were screened as weighted independent variables (n=46) are listed in Table 1 and those included in the final prognostic models (n=26) are listed in Table 2.

TABLE 1

Pre-Operative Parameters Screened as Potential Independent Variables

| | |
|---|---|
| Height (cm) | IVC Filter |
| Weight (kg) | Bariatric Procedure Planned |
| BMI | Age |
| Gender | Abdominal Hernia |
| African American | Alcohol Use |
| Angina | Hispanic |
| Asian | Asthma |
| Caucasian | Back Pain |
| Native American | Cholelithiasis |
| Mental Health Diagnosis | Pacific islander/Hawaiian |
| Other Race | Congestive Heart Failure |
| Cholecystectomy | Depression |
| Cholecystectomy with Common GERD | Bile Duct Exploration |
| Hypertension | Endoscopic Examination |
| Liver Disease | Gastrectomy Partial |
| Musculoskeletal Pain | Gastrectomy Total |
| Obesity | Hypoventilation Syndrome |
| Hiatal Hernia Repair | Psychological Impairment |
| Liver Biopsy | Pulmonary Hypertension |
| Lysis of Adhesions | Stress Urinary Incontinence |
| Small Bowel Resection | Tobacco Use |
| Umbilical Hernia Repair | Full Time Employment |
| Ventral Hernia Repair | Sex |

TABLE 2

Independent Variables Used in the SMART Bariatric Models

| | |
|---|---|
| Height (cm) | Age |
| Abdominal Hernia | Hypertension |
| African American | Operation |
| Alcohol Use | Liver Disease |
| Angina | Mental Health Diagnosis |
| Asthma | Musculoskeletal Pain |
| Back Pain | Obesity |
| Hypoventilation Syndrome | Congestive Heart Failure |
| Psychological Impairment | Caucasian |
| Employment | Pulmonary Hypertension |
| Cholelithiasis | Stress Urinary Incontinence |
| Depression | Weight (kg) |
| GERD | Gender |

Model fit for continuous and dichotomous dependent variables is displayed in Table 3. For weight and weight loss, $r^2$ values were 0.910, 0.813, 0.725, 0.638, and 0.613 in baseline models that predicted these continuous dependent variables at 2, 6, 12, 18, and 24 months post-operatively, respectively. ROC AUC for models predicting dichotomous dependent variables ranged from 0.985 for cholelithiasis at 2 months to 0.599 for Surgeon Follow-up/Support group attendance at 12 months. ROC AUCs for dichotomous models at 24 months post-operatively were 0.949 (cholelithiasis), 0.926 (diabetes), 0.804 (GERD), 0.858 (Hypertension), 0.941 (Liver Disease), 0.827 (Obstructive Sleep Apnea), 0.872 (Congestive Heart Failure), 0.921 (Abdominal Hernia), and 0.620 (Surgeon Follow-up/Support Group Attendance).

TABLE 3

| Observation | 2 Months | 6 Months | 12 Months | 18 Months | 24 Months |
|---|---|---|---|---|---|
| Number of patients | 120,909 | 75,130 | 42,410 | 15,387 | 11,014 |
| Continuous Dependent Variables: (r-squared) | | | | | |
| Weight/Weight Loss | 0.910 | 0.813 | 0.725 | 0.638 | 0.613 |
| Dichotomous Dependent Variables: (ROC/AUC) | | | | | |
| Cholelithiasis | 0.985 | 0.975 | 0.967 | 0.957 | 0.949 |
| Diabetes Mellitus | 0.956 | 0.940 | 0.933 | 0.930 | 0.926 |
| GERD | 0.898 | 0.860 | 0.829 | 0.818 | 0.804 |
| Hypertension | 0.913 | 0.891 | 0.874 | 0.869 | 0.858 |
| Liver Disease | 0.963 | 0.956 | 0.950 | 0.940 | 0.941 |
| Obstructive Sleep Apnea | 0.887 | 0.858 | 0.837 | 0.841 | 0.827 |
| Congestive Heart Failure | 0.881 | 0.878 | 0.883 | 0.883 | 0.872 |
| Abdominal Hernia | 0.971 | 0.960 | 0.947 | 0.935 | 0.921 |
| Surgeon Follow-up/Support Group Attendance | 0.597 | 0.600 | 0.599 | 0.603 | 0.620 |
| Any Adverse Event | | 0.683 | 0.683 | | |

Models for the complications of nausea and vomiting, intra-abdominal complications, and organ failure and sepsis were not successful because low event rates caused a quasi-separation of points. Grouping all occurrences of these adverse events into an Any Adverse Event category resulted in a receiver operating characteristic (ROC) area under the curve (AUC) of 0.683 for both the 0-6 month and 6-12 month periods.

Predicted versus observed outcomes validation data is listed in Table 4. Models from pre-operative data that predicted weight and weight loss were validated at 2, 6, 12, 18, and 24 months after surgery with Pearson Correlation Coefficients of 0.959, 0.932, 0.875, 0.837, and 0.811, respectively. Validation of pre-operative data models for dichotomous dependent variables included median sensitivity of 79.2% (range 25.0% to 98.30%) and median specificity of 97.42%% (range 80.27% to 99.99%). Models that predicted diabetes mellitus, hypertension, obstructive sleep apnea, liver disease, GERD, cholelithiasis, abdominal hernia, congestive heart failure, and bariatric surgeon follow-up/support group attendance at 24 months post-operatively were validated at sensitivities of 60.28%, 79.56%, 50.76%, 44.77, 86.93%, 75.27%, 77.58%, 25%, and 0.23%, respectively. Specificities were 93.97%, 79.3%, 90.95%, 86.65%, 97.21%, 99.1%, 98.05%, 99.4%, and 99.9%, respectively.

TABLE 4

| Observation | 2 Months | 6 Months | 12 Months | 18 Months | 24 Months |
|---|---|---|---|---|---|
| Number of patients | 120,909 | 75,130 | 42,410 | 15,387 | 11,014 |
| Continuous Dependent Variables: Pearson Correlation Coefficient | | | | | |
| Weight/Weight Loss | 0.959 | 0.932 | 0.875 | 0.837 | 0.811 |
| Dichotomous Dependent Variables: (ROC/AUC) | | | | | |
| Cholelithiasis | | | | | |
| Sensitivity | 97.13 | 4.7 | 91.78 | 90.94 | 86.93 |
| Specificity | 98.83 | 98.34 | 97.62 | 97.42 | 97.21 |
| Diabetes Mellitus | | | | | |
| Sensitivity | 98.39 | 74.87 | 72.14 | 69.14 | 60.28 |
| Specificity | 88.59 | 91.85 | 91.59 | 91.36 | 93.97 |
| GERD | | | | | |
| Sensitivity | 95.12 | 74.81 | 49.82 | 47.32 | 44.77 |
| Specificity | 81.05 | 80.27 | 87.07 | 87.25 | 86.65 |
| Hypertension | | | | | |
| Sensitivity | 92.44 | 92.61 | 77.91 | 79.15 | 79.56 |
| Specificity | 85.21 | 74.58 | 80.92 | 80.02 | 79.3 |
| Liver Disease | | | | | |
| Sensitivity | 88.55 | 85.22 | 84.79 | 79.39 | 77.58 |
| Specificity | 99.2 | 98.86 | 98.41 | 98.47 | 98.05 |
| Obstructive Sleep Apnea | | | | | |
| Sensitivity | 73.99 | 87.57 | 64.06 | 59.05 | 50.76 |
| Specificity | 93.68 | 87.64 | 88.01 | 89.94 | 90.95 |
| Congestive Heart Failure | | | | | |
| Sensitivity | 40.35 | 40.62 | 37.61 | 42.47 | 25 |
| Specificity | 99.84 | 99.79 | 99.71 | 99.68 | 99.4 |
| Abdominal Hernia | | | | | |
| Sensitivity | 93.31 | 90.03 | 85.99 | 79.2 | 75.27 |
| Specificity | 99.56 | 99.45 | 99.16 | 99.27 | 99.1 |
| Surgeon Follow-up/Support Group Attendance | | | | | |
| Sensitivity | 0.38 | 0.05 | 0.19 | 0 | 0.23 |
| Specificity | 99.87 | 99.98 | 99.94 | 99.89 | 99.9 |

TABLE 4-continued

| Observation | 2 Months | 6 Months | 12 Months | 18 Months | 24 Months |
|---|---|---|---|---|---|
| Any Adverse Event | | | | | |
| Sensitivity | | 0.52 | 0.51 | | |
| Specificity | | 99.92 | 99.92 | | |

For Any Adverse Event, specificity for both 0-6 months and 6-12 months was 99.92% but sensitivity was only 0.52% and 0.51%, respectively, for those intervals.

Accordingly, this invention provides prospectively validated models that predict, from pre-operative data in individual patients, weight loss and the persistence and/or resolution of morbid obesity co-morbidities two years in advance following ORYGB versus LAPRYGB versus AGB versus SLEEVE or versus DS. This advance knowledge enables morbidly obese patients and their providers to choose objectively whether or not to undergo bariatric surgery, and which operation best resolves weight-related medical conditions in each individual.

Example 3: Predicting Outcomes in Individual Patients Before Undergoing Bariatric Surgery Patient characteristics including age, abdominal hernia, African American race, Alcohol Use, Angina assessment, Asthma, Back Pain, CH), Caucasian, Cholelithiasis, Depression, GERD, Gender, Height (cm), Hypertension, Intercept, Liver Disease, Mental Health diagnosis, Musculoskeletal disease, Obesity Hypoventilation syndrome, Psychosocial Impairment, Pulmonary Hypertension, Stress Urinary Incontinence, Weight (Kg), full time employment, and treatment were obtained and entered into a network system for predicting post-operative outcomes of bariatric surgeries. Using predictive models for open gastric bypass, laparoscopic gastric bypass, adjustable gastric band, sleeve gastrectomy, and duodenal switch, an individual patient's baseline parameters were analyzed. Table 5 provides results from the model predictions for the patient.

TABLE 5

| Surgery | Predicted Outcome, Months After Surgery | | | | |
|---|---|---|---|---|---|
| | 2 | 6 | 12 | 18 | 24 |
| Abdominal Hernia[a] | | | | | |
| Adjustable Gastric Banding | 1 | 2 | 3 | 3 | 3 |
| Duodenal Switch | 1 | 6 | 25 | 40 | 30 |
| Laparoscopic RYGB | 1 | 2 | 3 | 3 | 3 |
| Open RYGB | 2 | 3 | 6 | 10 | 10 |
| Sleeve Gastrectomy | 1 | 3 | 6 | 8 | 6 |
| Congestive Heart Failure[a] | | | | | |
| Adjustable Gastric Banding | 12 | 9 | 8 | 13 | 5 |
| Duodenal Switch | 29 | 18 | 12 | 20 | 11 |
| Laparoscopic RYGB | 15 | 10 | 8 | 11 | 5 |
| Open RYGB | 13 | 9 | 7 | 14 | 4 |
| Sleeve Gastrectomy | 15 | 10 | 8 | 14 | 4 |
| Cholelithiasis[a] | | | | | |
| Adjustable Gastric Banding | 1 | 3 | 7 | 1 | 2 |
| Duodenal Switch | 26 | 38 | 60 | 25 | 21 |
| Laparoscopic RYGB | 2 | 3 | 8 | 2 | 2 |
| Open RYGB | 1 | 2 | 5 | 1 | 2 |
| Sleeve Gastrectomy | 3 | 5 | 12 | 3 | 3 |
| GERD[a] | | | | | |
| Adjustable Gastric Banding | 4 | 5 | 5 | 7 | 8 |
| Duodenal Switch | 5 | 8 | 6 | 9 | 12 |
| Laparoscopic RYGB | 3 | 3 | 3 | 4 | 5 |
| Open RYGB | 3 | 4 | 5 | 6 | 9 |
| Sleeve Gastrectomy | 4 | 5 | 5 | 7 | 9 |
| Glucose Metabolism[a] | | | | | |
| Adjustable Gastric Banding | 29 | 36 | 20 | 16 | 15 |
| Duodenal Switch | 27 | 26 | 8 | 8 | 5 |
| Laparoscopic RYGB | 30 | 29 | 12 | 8 | 8 |
| Open RYGB | 31 | 30 | 16 | 12 | 11 |
| Sleeve Gastrectomy | 29 | 29 | 13 | 11 | 9 |
| Hypertension[a] | | | | | |
| Adjustable Gastric Banding | 48 | 76 | 50 | 13 | 46 |
| Duodenal Switch | 31 | 50 | 18 | 4 | 17 |
| Laparoscopic RYGB | 33 | 52 | 24 | 4 | 21 |
| Open RYGB | 39 | 59 | 34 | 9 | 32 |
| Sleeve Gastrectomy | 37 | 60 | 30 | 7 | 27 |
| Liver Disease[a] | | | | | |
| Adjustable Gastric Banding | 1 | 1 | 1 | 1 | 0 |
| Duodenal Switch | 4 | 9 | 7 | 2 | 2 |
| Laparoscopic RYGB | 1 | 1 | 2 | 1 | 0 |
| Open RYGB | 3 | 4 | 4 | 1 | 1 |
| Sleeve Gastrectomy | 2 | 2 | 2 | 1 | 1 |
| Obstructive Sleep Apnea[a] | | | | | |
| Adjustable Gastric Banding | 94 | 96 | 95 | 94 | 91 |
| Duodenal Switch | 95 | 96 | 94 | 93 | 89 |
| Laparoscopic RYGB | 94 | 95 | 92 | 90 | 85 |
| Open RYGB | 95 | 95 | 94 | 91 | 86 |
| Sleeve Gastrectomy | 94 | 95 | 93 | 91 | 87 |
| Support Group Attendance[a] | | | | | |
| Adjustable Gastric Banding | 10 | 10 | 11 | 8 | 5 |
| Duodenal Switch | 17 | 18 | 19 | 16 | 11 |
| Laparoscopic RYGB | 14 | 15 | 16 | 12 | 9 |
| Open RYGB | 14 | 14 | 15 | 11 | 9 |
| Sleeve Gastrectomy | 13 | 13 | 14 | 11 | 7 |
| Weight | | | | | |
| Adjustable Gastric Banding | 362 | 343 | 327 | 315 | 308 |
| Duodenal Switch | 338 | 280 | 232 | 219 | 214 |
| Laparoscopic RYGB | 347 | 297 | 258 | 243 | 241 |
| Open RYGB | 342 | 396 | 253 | 231 | 235 |
| Sleeve Gastrectomy | 349 | 311 | 279 | 270 | 273 |
| Weight Loss | | | | | |
| Adjustable Gastric Banding | 38 | 57 | 73 | 85 | 92 |
| Duodenal Switch | 62 | 120 | 168 | 181 | 186 |
| Laparoscopic RYGB | 53 | 103 | 142 | 157 | 159 |
| Open RYGB | 58 | 104 | 147 | 169 | 165 |
| Sleeve Gastrectomy | 51 | 89 | 121 | 130 | 127 |
| BMI | | | | | |
| Adjustable Gastric Banding | 264 | 264 | 264 | 264 | 264 |
| Duodenal Switch | 264 | 264 | 264 | 264 | 264 |
| Laparoscopic RYGB | 264 | 264 | 264 | 264 | 264 |
| Open RYGB | 264 | 264 | 264 | 264 | 264 |
| Sleeve Gastrectomy | 264 | 264 | 264 | 264 | 264 |

[a]Numbers are the % probability of having that condition at that time.

What is claimed is:

1. A computer-implemented method for selecting and implementing a patient-specific bariatric surgery, the method comprising:
   receiving a baseline data set of a patient, the baseline data set including at least age, comorbidities, and employment for the patient;
   comparing the patient data set to a plurality of reference patient data sets to identify similar patient data sets in the plurality of reference patient data sets, wherein said comparison comprises linear regression modeling of independent variables for weight and weight loss as dependent variables, and logistic regression modeling of independent variables for comorbidities as dependent variables, wherein the independent variables comprise at least one of age or employment and wherein the reference patient data sets comprise patients receiving treatments with a plurality of bariatric surgeries;

identifying similar patient datasets from the reference patient data sets comprising a target treatment outcome associated with the plurality of bariatric surgeries;

calculating, for each of the plurality of bariatric surgeries, a probability of achieving the target treatment outcome for the patient; and selecting and implementing one of a plurality of a bariatric surgery devices for the patient based on the calculated probability of achieving the target treatment outcome, wherein the selected bariatric surgery device comprises an adjustable gastric band, intragastric balloon, transpyloric bulb, gastric emptying device, or electrical stimulator.

2. The computer-implemented method of claim 1, wherein the comorbidities comprise diabetes mellitus, hypertension, obstructive sleep apnea, liver disease, GERD, cholelithiasis, abdominal hernia, or congestive heart failure.

3. A system for selecting and implementing a patient-specific bariatric surgery for a patient, the system comprising:

one or more processors; and a memory storing instructions that, when executed by the one or more processors, cause the system to perform operations comprising:

receiving a baseline data set of a patient, the baseline data set including at least age, comorbidities, and employment for the patient;

comparing the patient data set to a plurality of reference patient data sets to identify similar patient data sets in the plurality of reference patient data sets, wherein said comparison comprises linear regression modeling of independent variables for weight and weight loss as dependent variables, and logistic regression modeling of independent variables for comorbidities as dependent variables, wherein the independent variables comprise at least one of age or employment and wherein the reference patient data sets comprise patients receiving treatments with a plurality of bariatric surgeries;

identifying similar patient data sets from the reference patient data sets comprising a target treatment outcome associated with the plurality of bariatric surgeries;

calculating, for each of the plurality of bariatric surgeries, a probability of achieving the target treatment outcome for the patient; and selecting and implementing one of a plurality of a bariatric surgery devices for the patient based on the calculated probability of achieving the target treatment outcome, wherein the selected bariatric surgery device comprises an adjustable gastric band, intragastric balloon, transpyloric bulb, gastric emptying device, or electrical stimulator.

* * * * *